United States Patent

Okamoto et al.

[11] Patent Number: 6,046,261
[45] Date of Patent: Apr. 4, 2000

[54] PIPERIDINE COMPOUND

[75] Inventors: Kazusige Okamoto, Ashiya; Motohiko Sammizzo, Kyoto; Mitsuo Shimode, Osaka, all of Japan

[73] Assignee: Sumitomo Chemical Company, Limited, Osaka, Japan

[21] Appl. No.: 09/131,505

[22] Filed: Aug. 10, 1998

[30] Foreign Application Priority Data

Aug. 11, 1997 [JP] Japan ..................... 9-216387

[51] Int. Cl.$^7$ ...................... C08K 5/3435; C07D 211/40
[52] U.S. Cl. ............................ 524/102; 546/188
[58] Field of Search ............... 524/102; 546/188

[56] References Cited

U.S. PATENT DOCUMENTS

| | | | |
|---|---|---|---|
| 4,105,625 | 8/1978 | Minagawa et al. | 260/45.8 N |
| 4,124,564 | 11/1978 | Minagawa et al. | 260/45.8 N |
| 4,219,463 | 8/1980 | Minagawa et al. | 260/45.8 N |
| 4,316,611 | 2/1982 | Stokes et al. | 273/85 D |
| 4,325,853 | 4/1982 | Acharya et al. | 524/272 |
| 4,338,244 | 7/1982 | Hinsken et al. | 524/109 |
| 5,175,312 | 12/1992 | Dubs et al. | 549/307 |
| 5,216,053 | 6/1993 | Jones et al. | 524/114 |
| 5,252,643 | 10/1993 | Nesvadba | 524/111 |

FOREIGN PATENT DOCUMENTS

| | | |
|---|---|---|
| 0 589 839 | 9/1993 | European Pat. Off. |
| 0 591 101 | 9/1993 | European Pat. Off. |
| 43 16 622 | 11/1993 | Germany. |
| 43 16 876 | 11/1993 | Germany. |
| 52-100543 | 8/1977 | Japan. |
| 52-112648 | 9/1977 | Japan. |

Primary Examiner—John Kight
Assistant Examiner—Charanjit S. Aulakh
Attorney, Agent, or Firm—Pillsbury Madison & Sutro LLP

[57] ABSTRACT

A piperidine compound having excellent blooming resistance represented by the formula (I)

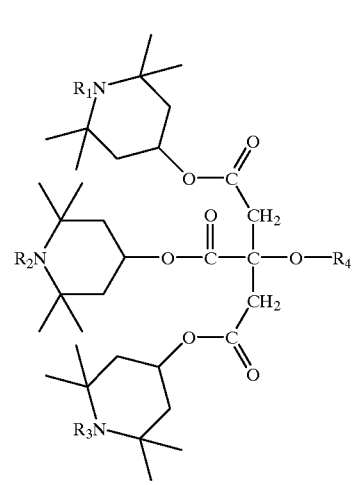

(wherein, $R_1$, $R_2$ and $R_3$ each independently represent a hydrogen atom, lower alkyl group, cycloalkyl group having 5 to 7 carbon atoms or an acyl group having 2 to 18 carbon atoms. $R_4$ represents an acyl group having 2 to 18 carbon atoms.) is provided, and a method for producing the piperidine compound and use thereof as a stabilizer for an organic material are also provided.

10 Claims, 1 Drawing Sheet

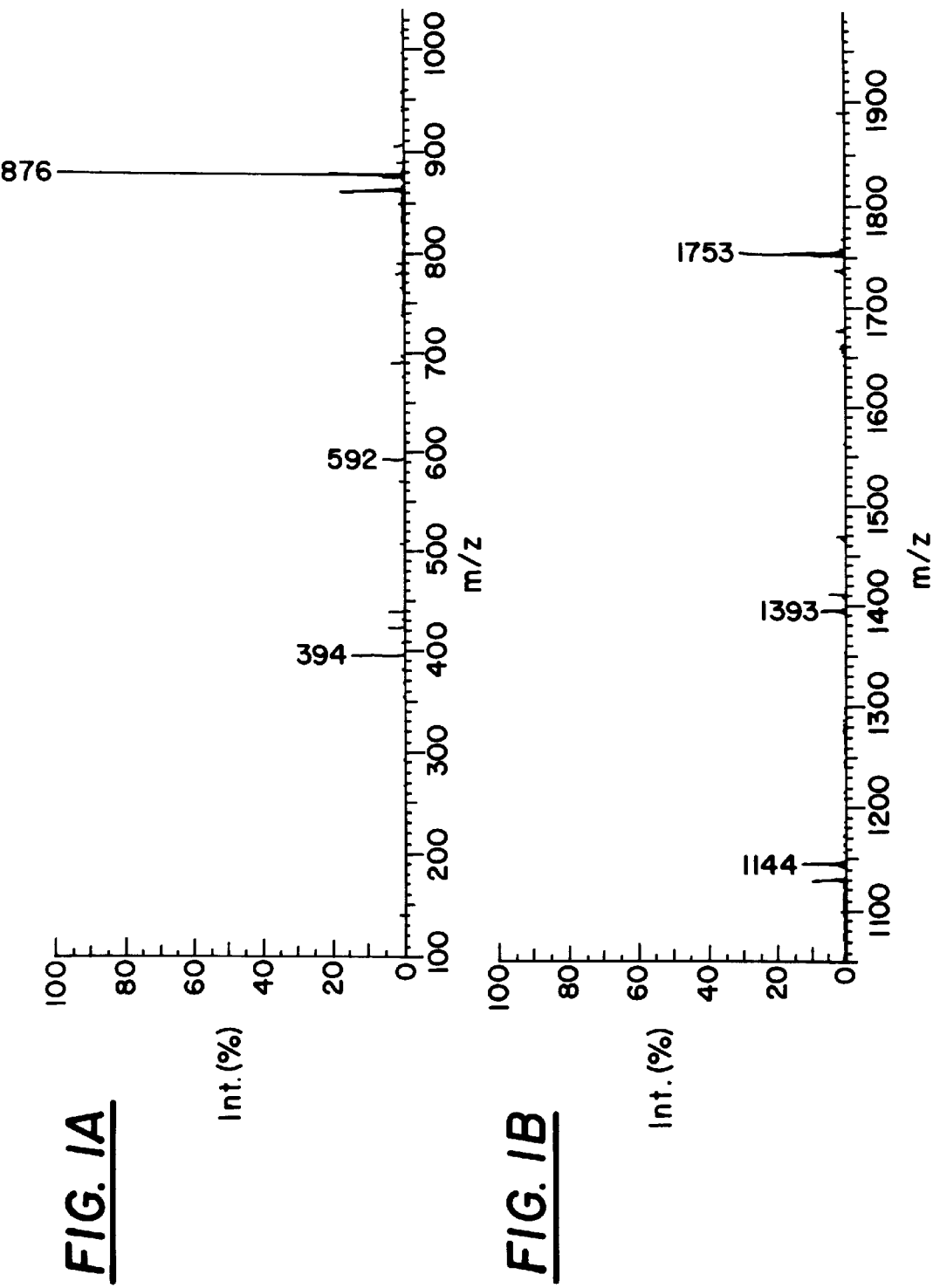
FIG. IA
FIG. IB

PIPERIDINE COMPOUND

The present invention relates to a novel PIPERIDINE compound, a method for producing the same, and use thereof as a stabilizer for an organic material.

It is well known that organic materials such as thermoplastic resins, thermosetting resins, natural or synthetic rubber are degraded by light, and physical properties thereof are remarkably lowered accompanying softening, embrittlement, discoloration and the like.

For preventing the degradation by light as described above, carboxylates of piperidinol, such as bis(2,2,6,6-tetramethyl-4-piperidyl)sevacate and tris(2,2,6,6-tetramethyl-4-piperidyl) 2-hydroxy-1,2,3-propanetricarboxylate, are suggested (for example, JP-A-52-112648, and the like).

However, the carboxylates as described above were not satisfactory since they have a problem of blooming out when they are contained in an organic material.

The present inventors have intensively studied to find a carboxylate of piperidinol having excellent blooming resistance. As a result, it was found that specific carboxylate, 2-acyloxy-1,2,3-tricarboxylate, has remarkably excellent blooming resistance. Thus, the present invention was completed.

The present invention provides a piperidine compound having excellent blooming resistance represented by the formula (I)

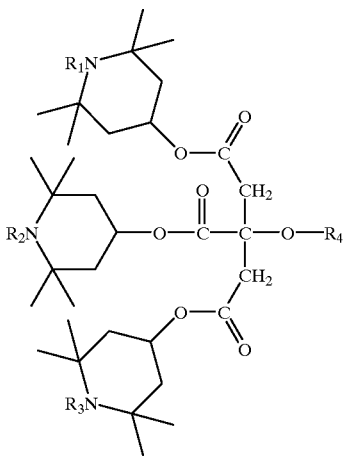

(I)

(wherein, $R_1$, $R_2$ and $R_3$ each independently represent a hydrogen atom, lower alkyl group, cycloalkyl group having 5 to 7 carbon atoms or an acyl group having 2 to 18 carbon atoms. $R_4$ represents an acyl group having 2 to 18 carbon atoms.).

The present invention also provides a method for producing the piperidine compound of formula (I), and use thereof as a stabilizer for an organic material.

BRIEF DESCRIPTION OF DRAWING

In the drawing, FIG. 1 shows a FD-MS spectrum of the compound obtained in Example 1.

In the piperidine compound represented by the formula (I) of the present invention, $R_1$, $R_2$ and $R_3$ each independently represent a hydrogen atom, lower alkyl group, cycloalkyl group having 5 to 7 carbon atoms or an acyl group having 2 to 18 carbon atoms, and $R_4$ represents an acyl group having 2 to 18 carbon atoms.

Examples of the lower alkyl group as $R_1$, $R_2$ and $R_3$ include methyl, ethyl, n-propyl, i-propyl, n-butyl, t-butyl, pentyl, t-pentyl and the like, and typical examples of the cycloalkyl group having 5 to 7 carbon atoms include cyclopentyl, cyclohexyl, methylcyclohexyl, cycloheptyl and the like.

Examples of the acyl group having 2 to 10 carbon atoms as $R_1$, $R_2$, $R_3$ or $R_4$ include groups represented by the formula (II)

(II)

(wherein, $R_5$ represents an alkyl group having 2 to 17 carbon atoms, a cycloalkyl group having 3 to 9 carbon atoms which may be optionally substituted with a lower alkyl group and/or lower alkenyl group, a phenyl group having 6 to 14 carbon atoms which may be optionally substituted with a lower alkyl group and/or hydroxyl group, or a phenylalkylene group having 7 to 17 carbon atoms in which the phenyl group and/or hydroxyl group.)
and the like.

Examples of the alkyl group having 2 to 17 carbon atoms as $R_5$ include lower alkyl groups, such as ethyl, n-propyl, i-propyl, n-butyl, t-butyl, pentyl and t-pentyl, and in addition, hexyl, heptyl, octyl, 2,4,4-trimethylpentyl, 2-ethylhexyl, 1,1,3,3-tetramethylbutyl, nonyl, decyl, dodecyl, tetradecyl, hexadecyl, heptadecyl and the like.

Examples of the cycloalkyl group having 3 to 9 carbon atoms which may be optionally substituted with a lower alkyl group and/or lower alkenyl group as $R_5$ include cyclopropyl, 2,2-dimethylcyclopropyl, 2,2,4,4-tetramethylcyclopropyl, 2,2-dimethyl-3-(2,2-dihalovinyl) cyclopropyl, 2,2-dimethyl-3-i-butenylocyclopropyl, cyclopentyl, methylcyclopentyl, cyclohexyl, methylcyclohexyl, butylcyclohexy, cycloheptyl and the like. Example of the lower alkenyl group as the substituent include vinyl, dihalovinyl, propenyl, butenyl, i-butenyl and the like.

Examples of the phenyl group having 6 to 14 carbon atoms which may be optionally substituted with a lower alkyl group and/or hydroxyl group, as $R_5$, include an unsubstituted phenyl, phenyl substituted with ethyl, n-propyl, i-propyl, n-butyl, t-butyl, pentyl and t-pentyl, hydroxyphenyl, 3-t-butyl-4-hydroxy-5-methylphenyl, 3,5-di-t-butyl-4-hydroxyphenyl and the like.

Examples of the phenylalkylene group having 7 to 17 carbon atoms, as $R_5$, in which the phenyl group may be optionally substituted with a lower alkyl group and/or hydroxyl group include alkylenes having 2 to 3 carbon atoms substituted with the same phenyl group as described above.

Among other, $R_1$, $R_2$ and $R_3$ are preferably hydrogen or lower alkyl, and more preferably hydrogen or methyl, particularly hydrogen.

$R_4$ is preferably an acyl group represented by the formula (II), and, among other, an acyl group in which $R_5$ is selected from an alkyl group having 2 to 17, particularly 4 to 17 carbon atoms, a cycloalkyl group having 7 to 9 carbon atoms which may be optionally substituted with a lower alkyl group and lower alkenyl group, a phenyl group having 6 to 14 carbon atoms which may be optionally substituted with a lower alkyl group and hydroxyl group, a phenylalkylene group having 7 to 17 carbon atoms in which the phenyl group may be optionally substituted with a lower alkyl group and/or hydroxyl group, and the like. Particularly preferable examples, as $R_4$, include an acyl group in which $R_5$ is selected from alkyl groups having 8 to 17 carbon atoms such as 2,4,4-trimethylpentyl, 2-ethylhexyl, 1,1,3,3-tetramethylbutyl, decyl, dodecyl, tetradecyl, hexadecyl, heptadecyl and the like, cycloalkyl groups such as 2,2,4,4-tetramethylcyclopropyl, 2,2dimethyl-3-(2,2-dihalovinyl) cyclopropyl, 2,2-dimethyl-3-i-butenylcyclopropyl and the like, phenyl groups such as phenyl, 3-t-butyl-4-hydroxy-5-methylphenyl, 3,5-di-t-butyl-4-hydroxyphenyl and the like, phenylalkylene groups such as (3-t-butyl-4-hydroxy-5-methylphenyl)ethyl, (3,5-di-t-butyl-4-hydroxyphenyl)ethyl, and the like.

The piperidine compound (I) of the present invention can be produced, for example, by acylating piperidyl hydroxycarboxylate represented by the formula (III):

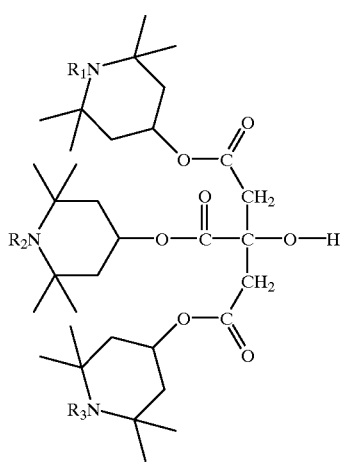

(III)

(wherein, $R_1$, $R_2$ and $R_3$ are as defined above.)
with an acylating agent represented by the formula (IV):

(IV)

(wherein, $R_4$ is as defined above. X represents a halogen atom, $-OR_7$, $-OC(O)R_5$ or $-NR_8R_9$, wherein $R_7$, $R_8$ and $R_9$ represent a hydrogen atom or lower alkyl group.).

The acylation reaction can be carried out according to a known method, for example, a method described in "Shin Jikken Kagaku Koza 14, Synthesis and Reaction of Organic Compounds (II)", pp. 1002 to 1022 (Dec. 20, 1977, published by Maruzen Co., Ltd.), and the like.

The reaction is carried out in the presence or absence of a solvent. When a solvent is used, examples of the solvent include aromatic hydrocarbons such as benzene, toluene, xylene, ethylbenzen, nitrobenzene and the like, aliphatic hydrocarbons such as hexane, heptane, ocatane and the like, ethers such as diethyl ether, dibutyl other, tetrahydrofuran, tetrahydrofuran, 1,4-dioxane and the like, halogenated hydrocarbons such as chloroform, carbon tetrachloride, monochlorobenzene, dichloromethane, dichloroethane, dichlorobenzene and the like.

When a solvent is used, the solvent is used in an amount usually from 3 to 50-fold by weight, preferably from 3 to 15-fold by weight based on piperidyl hydroxycarboxylate (III).

The acylating agent is used in an amount usually from 1 to 5-fold by weight, preferably from 1 to 2-fold by weight based on piperidyl hydroxycarboxylate (III). When two or more acylating agents (carboxylic acids) in which $R_4$ differs are used, a mixture of them may be reacted, or they may be reacted sequentially.

The acylation reaction is carried out at a temperature usually from 0 to 150° C., preferably from 10 to 80° C.

As the acylating agent, an acid halide is preferably used. In this case, the acid halide is preferably reacted in the presence of a dehydrohalogenating agent such as amines, piridines, pyrrolidines, amides and the like.

The amides may be any of primary amines, secondary amines and tertiary amines. Examples thereof include t-butylamine, t-pentylamine, t-hexylamine, t-octylamine, di-t-butylamine, di-t-pentylamine, di-t-hexyamine, di-t-ocytlamine, trimethylamine, triethylamine, N.N-dimethylaniline, N,N-diethylaniline, and the like, and triethylamine is preferable.

Examples of piridines include piridine, 4-aminopiridine, 4-(N,N-dimethylamino)piridine, picoline and the like, and piridine is preferable. As pyrrolidines, for example, 1-methyl-2-piddolidine and the like are listed.

Examples of amides include N,N-dimethylformamide, N,N-dimethylacetoamide and the like, and N,N-dimethylformamide is preferable.

When the dehydrohalogenating agent is used, it is used in an amount usually from 1 to 4-fold by equivalent, preferably from 1 to 2-fold by equivalent based on the acid halide.

After the reaction, the piperidine compound of the present invention can be optionally taken out from a reaction mixture by conducting neutralization, extraction, washing with water, distillation off of lower boiling point fractions, and the like. The piperidine compound taken out can also be further purified by purification means such as various chromatography, re-crystallization, distillation and the like.

Piperidyl hydroxycarboxylate (III) which is a raw material of the piperidine compound (I) of the present invention can be produced, for example, by allowing a lower alkyl ester of citric acid to react with one or more compounds selected from piperidinols represented by the formula (V):

(V)

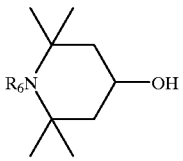

(wherein, $R_6$ represents a hydrogen atom, lower alkyl group or cycloalkyl group having 5 to 7 carbon atoms) according to a method described in JP-A No. 52-112648, etc. It can also be produced by reacting citric acid or an acid halide thereof with piperidinols (V) according to a known method.

Thus obtained piperidine compound (I) of the present invention is effective for stabilization against light degradation and the like of an organic material. Examples of the organic materials which can be stabilized by the present invention include, but are not limited to, the following compounds, and they can be stabilized alone or in combination of two or more.

(1) polyethylene, for example, high-density polyethylene (HDPE), low-density polyethylene (LDPE) and straight-chain low-density polyethylene (LLDPE)
(2) polypropylene
(3) methylepentene polymer
(4) EEA (ethylene/ethyl acrylate copolymer) resin
(5) ethylene/vinyl acetate copolymer resin
(6) polystyrenes, (for example, polystyrene, poly(p-methylstyrene) and poly(α-methylstyrene)
(7) AS (acrylonitrile/styrene copolymer) resin
(8) ABS (acrylonitrile/butadiene/styrene copolymer) resin (9) AAS (special acrylic rubber/acrylonitrile/styrene copolymer resin
(10) ACS (acrylonitrile/chlorinated polyethylene/styrene copolymer) resin
(11) chlorinated polyethylene, polychloroprene, chlorinated rubber
(12) polyvinyl chloride, polyvinylidene chloride
(13) methacrylic resin
(14) ethylene/vinyl alcohol copolymer resin
(15) fluororesin
(16) polyacetal
(17) grafted polyphenylene ether resin and polyphenylene sulfide resin
(18) polyurethane
(19) polyamide
(20) polyester resin, for example, polyethylene terephthalate and polybutylene terephthalate
(21) polycarbonate
(22) polyacrylate
(23) polysulfone, polyether ether ketone, polyether sulfone
(24) thermoplastic resin such as aromatic polyester resin, etc.
(25) epoxy resin
(26) diallyl phthalate prepolymer
(27) silicone resin
(28) unsaturated polyester resin
(29) acrylic-modified benzoguanamine resin
(30) benzoguanamine/melamine resin
(31) thermosetting resin such as urea resin, etc.
(32) polybutadiene
(33) 1,2-polybutadiene
(34) polyisoprene
(35) styrene/butadiene copolymer
(36) butadiene/acrylonitrile copolymer
(37) ethylene/propylene copolymer
(38) silicone rubber
(39) epichlorohydrin rubber
(40) acrylic rubber
(41) natural rubber
(42) chlorinated rubber paint
(43) polyester resin paint
(44) urethane resin paint
(45) epoxy resin paint
(46) acrylic resin paint
(47) vinyl resin paint
(48) aminoalkyd resin paint
(49) alkyd resin
(50) nitrocellulose resin paint
(51) oil-based paint Among them, the thermoplastic resin, particularly polyolefin such as polyethylene (e.g. HDPE, LDPE, LLDPE, etc.) and polyolefin (e.g. polypropylene, etc.) is more suitable to be stabilized by the present invention.

The polyolefins are not specifically limited. For example, they may be those obtained by the radical polymerization or those produced by the polymerization using a catalyst containing a metal of Group IVb, Vb, VIb or VIII of the periodic table. The catalyst containing such a metal may be a metal complex which is coordinated by one or more ligands, for example, oxide which is coordinated by a π or σ bond, halogenated compound, alcoholate, ester, aryl and the like, and these complexes may be used as they are, or a base material such as magnesium chloride, titanium chloride, alumina, silicon oxide, etc. may carry the complexes.

As the polyolefin, for example, there are preferably used those produced by using Ziegler-Natta catalyst, TNZ catalyst, metallocene catalyst, Phillips catalyst, Brookart catalyst and the like.

When the organic material is stabilized by containing the piperidine compound (I) of the present invention, the piperidine compound are normally formulated in an amount of about 0.01 to 5 parts by weight. When the amount is less than 0.01 parts by weight, the stabilizing effect may not be sufficient, necessarily. On the other hand, even when the amount exceeds 5 parts by weight, an improvement of the effect corresponding to the increase in the amount used may not be obtained and this may be economically disadvantageous.

When the piperidine compound (I) of the present invention are contained in the organic material, if desired, there can also be contained one or more other additives such as phenol antioxidant, sulfur antioxidant, phosphorous antioxidant, ultraviolet absorber, photostabilizer, peroxide scavenger, polyamide stabilizer, hydroxylamine, lubricant, plasticizer, flame retardant, nucleating agent, metal inactivating agent, antistatic agent, pigment, filler, pigment, antiblocking agent, surfactant, processing aid, foaming agent, emulsifier, brightener, calcium stearate, neutralizing agent (e.g. hydrotalcite, etc.), coloring modifier (e.g. 9,10-dihydro-oxo-10-phosphophenanthrene-10-oxide, etc.) and co-stabilizer (e.g. benzofurans, indolines, etc. described in U.S. Pat. Nos. 4,325,853, 4,338,244, 5,175,312, 5,216,053, 5,242,643 and 4,316,611, DE-A-4,316,622 and 4,316,876, and EP-A-589,839 and 591,101). These additives can be formulated together with the piperidine compound, and/or can be formulated in the stage other than a stage where the piperidine compound are formulated.

Examples of the phenol antioxidant include the following.
(1) Examples of alkylated monophenol
2,6-di-t-butyl-4-methylphenol, 2,4,6-tri-t-butylphenol, 2,6-di-t-butyl-4-butylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4, 6-dimethylphenol, 2,6dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6'-(1'-methylheptadecyl-1'-yl)phenol, 2,4 -dimethyl-6-(1'-methyltridecyl-1'-yl)phenol and a mixture thereof.

(2) Examples of alkylthiomethylphenol
2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and a mixture thereof.

(3) Examples of hydroquinone and alkylated hydroquinone
2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-di-t-butyl-4-hydroxyphenyl)adipate and a mixture thereof.

(4) Examples of tocopherol
α-tocopherol, β-tocopherol, γ-tocopherol, δ-tocopherol and a mixture thereof.

(5) Examples of hydroxylated thiodiphenyl ether
2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenol)disulfide and the like.

(6) Examples of alkylidenebisphenol and derivative thereof
2,2'-methylenebis(4-methyl-6-t-butylphenol), 2,2'-methylenebis(4-ethyl-6-t-butylphenol), 2,2'-methylenebis

[4-methyl-6-(α-methylcyclohexyl)phenol], 2,2'-methylenebis(4-methyl-6-cyclohexylphenol), 2,2'-methylenebis(4-methyl-6-nonylphenol), 2,2'-methylenebis(4,6-di-t-butylphenol), 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[6-(αα-dimethylbenzyl)-4-nonylphenol)], 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 2,6-bis(3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, bis[3,3-bis-(3'-t-butyl-4'-hydroxyphenyl)butyrate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy- 3,5-di-t-pentylphenyl)ethyl]phenyl acrylate and a mixture thereof.

(7) Examples of O-, N- and S-benzyl derivative 3,5,3',5'-tetra-t-butyl-4,4'-dihydroxydebenzyl ether, octadodecyl-4-hydroxy-3,5-dimethylbenzylmercapto acetate, tris(3,5-di-t-butyl-4-hydroxybenzyl)amine, bis(4-t-butyl-3-hydroxy-2,6-dimethylbenzyl)dithioterephthalate, bis(3,5-di-t-butyl-4-hydroxybenzyl)sulfide, isooctyl-3,5-di-t-butyl-4-hydroxybenzylmercapto acetate and a mixture thereof.

(8) Examples of hydroxybenzylated malonate derivative dioatadecyl-2,2,2-bis(3,5-di-t-butyl-2-hydroxybenzyl)malonate, dioctadecyl-2-(3-t-butyl-4-hydroxy-5-methylbenzyl)malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate and a mixture thereof.

(9) Examples of aromatic hydroxybenzyl derivative 1,3,5-trimethyl-2,4,6-tris(3,5-di-t-butyl-4-hydroxybenzyl)benzene, 1,4-bis(3,5-di-t-butyl-4-hydroxybenzyl)-2,3,5,6-tetramethylbenzene, 2,4,6-tris(3,5-t-butyl-4-hydroxybenzyl)phenol and a mixture thereof.

(10) Examples of triazine derivative 2,4-bis(n-octylthio)-6-(4-hydroxy-3,5-di-t-butylanilino)-1,3,5-triazine, 2-n-octylthio-4,6-bis(4 -hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-hydroxy)-1,3,5-triazine, tris(4-t-butyl-3-hydroxy-2,6-diemthylbenzyl isocyanurate, tris(3,5-di-t-butyl-4-hydroxybenzyl)isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'-di-t-butyl-4'-hydroxycinnamoyloxy)ethyl]isocyanurate and a mixture thereof.

(11) Examples of benzyl phosphonate derivative dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonic acid monoester and a mixture thereof.

(12) Examples of acylaminophenol derivative anilide 4-hydroxylaurate, anilide 4-hydroxystearate, octyl-N-(3,5-di-t-butyl-4-hydroxyphenyl)carbamate and a mixture thereof.

Ester of β-(3,5-di-t-butyl-4-hydroxyphenyl)propionic acid and the following monohydric or polyhydric alcohol methanol, ethanol, octanol, octadecanol, ethylene glycol, 1,3-propanediol, 1,4-butanediol, 1,6-bexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(14) Ester of β-(5-t-butyl-4-hydroxy-3-methylphenyl) propionic acid and the following monohydric or polyhydric alcohol methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(15) Ester of β-(3,5-dicyclohexyl-4-hydroxyphenyl) propionic acid and the following monohydric or polyhydric alcohol methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(16) Ester of 3,5-t-butyl-4-hydroxyphenylacetic acid and the following monohydric or polyhydric alcohol methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(17) Examples of amine of β-(3,5-di-t-butyl-4-hydroxyphenyl)propionic acid

N,N'-bis[3-(3',5'-di-t-butyl-4'-hydroxyphenyl)propionyl] hydrazine, N,N'-bis[3-(3',5'-di-t-butyl-4'-hydroxyphenyl) propionyl]hexamethylenediamine, N,N'-bis[3-(3',5'-di-t-butyl-4'-hydroxyphenyl)propionyl]trimethylenediamine and a mixture thereof.

Examples of the sulfur antioxidant include:

dilauryl 3,3'-thiodipropionate, tridecyl 3,3'-thiodipropionate, dimyristyl 3,3'-thiodipropionate, distearyl 3,3'-thiodipropionate, lauryl stearyl 3,3'-thiodipropionate, neopentanetetrayltetrakis(3-lauryl thiopropionate) and the like.

Examples of the phosphorous antioxidant include the following:

triphenyl phosphite, tris(nonylphenyl)phosphite, tris(2,4-di-t-butylphenyl)phosphite, trilauryl phosphite, trioctadocyl phosphite, distearyl pentaerythritol diphosphite, diisodecyl pentaerythritol diphosphite, bis(2,4-di-t-butylphenyl) pentaerythritol diphosphite, bis(2,4-di-t-butyl-6-methylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, bis(2,4,6-tri-t-butylphenyl)pentaerythritol diphosphite, tristearyl sorbitol triphosphite, tetrakis(2,4-di-t-butylphenyl)-4,4'-diphenylene diphosphite, 2,2'-methylenebis(4,6-di-t-butylphenyl)2-ethylhexyl phosphite, 2,2'-ethylidenebis(4,6-di-t-butylphenyl)fluoro phosphite, bis(2,4-di-t-butyl-6-methylphenyl)ethyl phosphite, bis(2,4-di-t-butyl-6-methylphenyl)methyl phosphite, (2,4,6-tri-t-butylphenyl)-5-ethyl-5-butyl-1,3,2-oxaphosphorinane, 2,2',2''-nitrilo[triethyl-tris(3,3',5,5'-tetra-t-butyl-1,1'-biphenyl-2,2'-diyl)phosphite and a mixture thereof Examples of the ultraviolet absorber include the following:

(1) Examples of salicylate derivative phenyl salicylate, 4-t-butylphenyl salicylate, 2,4-di-t-butylphenyl 3',5'-di-t-butyl-4'-hydroxybenzoate, 4-t-octylphenyl salicylate, bis(4-t-butylbenzoyl)resorcinol, benzoylresorcinol, hexadecyl 3',5'-di-t-butyl-4'-hydroxybenzoate, octadecyl 3',5'-di-t-butyl-4'-hydroxybenzoate, 2-methyl-4,6-di-t-butylphenyl 3',5'-di-t-butyl-4'-hydroxybenzoate and a mixture thereof (2) Examples of 2-hydroxybenzophenone derivative 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone and a mixture thereof (3) Examples of 2-(2'-hydroxyphenyl)benzotriazole 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxypheny)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl-5'-[2-(2-ethylhexyloxy)carbonylethyl]-2'-hydroxyphenyl]-5-chlorobenzotriazole, 2-[3'-t-butyl-2'-hydroxy-5'-(2-methoxycarbonylethyl)phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl]benzotriazole, 2-[3'-t-butyl-2'-hydroxy-5'-[2-(2-ethylhexyloxy)carbonylethyl]phenyl]benzotriazole, 2-[2-hydroxy-3-(3,4,5,6-tetrahydrophthalimidemethyl)-5-methylphenyl]benzotriazole, 2-(3',5'-di-t-butyl-2-hydroxyphenyl)-5-chlorobenzotriazole, mixture of 2-(3'-dodecyl-2'-hydroxy-5'-methylphenyl)benzotriazole and 2-[3'-t-butyl-2'-hydroxy-5'-(2-isooctyloxycarbonylethyl)phenyl]benzotriazole, 2,2'-methylenebis[6-(2H-benzotriazol-2-yl)-4-(1,1,3,3-tetramethylbutyl)phenol, 2,2'-methylenebis[4-t-butyl-6-(2H-benzotriazol-2-yl)phenol], condensate of poly(3-11)(ethylene glycol) and 2-[3'-t-butyl-2'-hydroxy-5'-(2-methoxycarbonylethyl)phenyl] benzotriazole, condensate of poly(3-11)(ethylene glycol) and methyl 3-[3-(2H-benzotriazol-2-yl)-5-t-butyl-4-hydroxyphenyl]propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl]propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenyl] propionic acid and a mixture thereof.

Examples of the photostabilizer include the following.

(1) Examples of hindered amine photostabilizer bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acrolyl-2,2,6,6-tetramethyl-4-piperidyl) 2,2-bis(3,5-di-t-butyl-4-hydroxybenzyl)-2-butylmalonato, bis(1,2,2,6,6-penatmethyl-4-piperidyl decanedioate, 2,2,6,6-tetramethyl-4-piperidyl methacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetrakis(2,2,6,6-tetramethyl-4-piperidyl) 1,2,3,4-butanetetracarboxylate, tetrakis(1,2,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-butanetetracarboxylic acid and 1,2,2,6,6-pentamethyl-4-piperidinol and 3,9-bis(2-hydroxy-1,1-dimethylethyl)-2,4,8,10-tetraoxaspiro[5,5]undecane, mixed esterified product of 1,2,3,4-butanetetracarboxylic acid and 2,2,6,6-tetramethyl-4-piperidinol and 3,9-bis(2-hydroxy-1,1-dimethylethyl)-2,4,8,10-tetraoxaspiro[5,5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino)hexamethylene ((2,2,6,6-tetramethyl-4-piperidyl)imino)], poly[(6-(1,1,3,3-tetramethylbutyl)imino-1,3,5-triazin-2,4-diyl) ((2,2,6,6-tetramethyl-4-piperidyl)imino)hexamethylene ((2,2,6,6-tetramethyl-4-piperidyl)imino)], polycondensate of N,N'-bis(2,2,6,6-tetramethyl-4-piperidyl)hexamethylenediamine and 1,2-bromoethane, N,N',4,7-tetrakis[4,6-bis(N-butyl-N-(2,2,6,6-tetramethyl-4-piperidyl)amino)-1,3,5-triazin-2-yl]-4,7-diazadecane-1,10 diamine, N,N',4-tris[4,6-bis(N-butyl-N-(2,2,6,6-tetramethyl-4-piperidyl)amino)-1,3,5-triazin-2-yl]-4,7-diazadecane-1,10 diamine, N,N',4,7-tetrakis[4,6-bis(N-butyl-N-(1,2,2,6,6-pentamethyl-4-piperidyl)amino)-1,3,5-triazin-2-yl]-4,7-diazadecane-1,10 diamine, N,N',4-tris[4,6-bis(N-butyl-N-(1,2,2,6,6-pentamethyl-4-piperidyl)amino)-1,3,5-triazin-2-yl]-4,7-diazadecane-1,10 diamine and a mixture thereof (2) Examples of acrylate photostabilizer ethyl α-cyano-β,β-diphenylacrylate, isooctyl α-cyano-β,β-diphenylacrylate, methyl α-carbomethoxycinnamate, methyl α-cyano-β-methyl-methoxycinnamate, butyl α-cyano-β-methyl-p-methoxycinnamate, methyl α-carbomethoxy-p-methoxycinnamate and N-(β-carbomethoxy-β-cyano-vinyl)-2-methylindoline and a mixture thereof (3) Examples of nickel photostabilizer nickel complex of 2,2'-thiobis-[4-(1,1,3,3-tetramethylbutyl)phenol], nickel dibutyldithiocarbamate, nickel salt of monoalkyl ester, nickel complex of ketoxime and a mixture thereof (4) Examples of oxamide photostabilizer 4,4'-dioctyloxyoxanilide, 2,2'-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-b-t-butyl-2'-ethoxyanilide, 2-ethoxy-5,4'-di-t-butyl-2'-ethyloxanilide and a mixture thereof (5) Examples of 2-(2-hydroxyphenyl)-1,3,5-triazine photostabilizer 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(4-methylphenyl)-1,3,5-triazine, 2-[2-hydroxy-4-(2-hydroxy-3-butyloxypropoxy)phenyl]-4,6-bis(2,4 -dimethylphenyl)-1,3,5-triazine, 2-[2-hydroxy-4-(2-hydroxy-3-octyloxyphenyl)-4,6-bis(2,4-dimethylphenyl)-1,3,5-triazine and a mixture thereof.

Examples of the metal inactivating agent include the following:

N,N'-diphenyloxamide, N-salicylal-N'-salicyloylhydrazine, N,N'-bis(salicyloyl)hydrazine, N,N'-bis(3,5-di-t-butyl-4-hydroxyphenylpropionyl)hydrazine, 3-salicyloylamino-1,2,4-triazole, bis(benzylidene)oxalyl dihydrazide, oxalinide, isophthaloyl dihydrazide, sebacoyl-bisphenyl hydrazide, N,N'-bis(salicyloyl)thiopropionyl dihydrazide and a mixture thereof Examples of the peroxide scavenger include ester of β-thiodipropionic acid, mercaptobenzoimidazole, zinc salt of 2-mercaptobenzoimidazole, zinc salt of dibutyldithiocarbamic acid, dioctadecyl disulfide, pentaerythritol tetrakis(β-dodecylmercapto)propionate and a mixture thereof.

Examples of the polyamide stabilizer include copper or divalent manganese salt of iodide or phosphorous compound and a mixture thereof.

Examples of the hydroxyamine include N,N-dibenzylhydroxyamine, N,N-diethylhydroxyamine, N,N-dioctylhydroxyamine, N,N-dilaurylhydroxyamine, N,N-ditetradecylhydroxyamine, N,N-dihexadecylhydroxyamine, N,N-dioctadecylhydroxyamine, N,N-dibenzylhydroxyamine, N,N-dibenzylhydroxyamine, N-hexadecyl-N-octadecylhydroxyamine, N-heptadecyl-N-octadecylhydroxyamine and a mixture thereof.

Examples of the neutralizing agent include calcium stearate, zinc stearate, magnesium stearate, hydrotalcite (basic magnesium aluminum hydroxycarbonate hydride), melamine, amine, polyamide, polyurethane and a mixture thereof.

Examples of the lubricant include aliphatic hydrocarbon (e.g. paraffin, wax, etc.), higher aliphatic acid having 8 to 22 carbon atoms, higher aliphatic acid (having 8 to 22 carbon atoms) metal (e.g. Al, Ca, Mg, Zn) salt, aliphatic alcohol having 8 to 22 carbon atoms, polyglycol, ester of higher fatty acid having 4 to 22 carbon atoms and aliphatic monohydric alcohol having 4 to 18 carbon atoms, higher aliphatic amide having 8 to 22 carbon atoms, silicone oil, resin derivative and the like.

Examples of the nucleating agent include the following:

sodium 2,2'-methylenebis(4,6-di-t-butylphenyl) phosphate, [phosphoric acid-2,2'-methylenebis(4,6-di-t-butylphenyl)] dihydroxyaluminum, bis[phosphoric acid-2,2'-methylenebis(4,6-di-t-butylphenyl)] dihydroxyaluminum, tris[phosphoric acid-2,2'-methylenebis(4,6-di-t-butylphenyl)] aluminum, sodium bis(4,6-di-t-butylphenyl)phosphate, benzoic acid metal salt such as sodium benzoate, aluminum p-t-butylbenzoate, 1,3:2,4-bis(O-benzylidene)sorbitol, 1,3:2,4-bis(O-ethylbenzylidene)sorbitol, 1,3:2,4-bis(O-methylbenzylidene)sorbitol, 1,3-O-3,4-dimethylbenzylidene-2,4-O-benzylidenesorbitol, 1,3-O-benzylidene-2,4-O-3,4-dimethylbenzylidene sorbitol, 1,3:2,4-bis(O-3,4-dimethylbenzylidene)sorbitol, 1,3-O-p-chlorobenzylidene-2,4-O-3,4-dimethylbenzylidene sorbitol, 1,3-O-3,4-dimethylbenzylidene-2,4-O-p-chlorobenzylidene sorbitol, 1,3:2,4-bis(O-p-chlorobenzylidene)sorbitol and a mixture thereof.

Examples of the filler include calcium carbonate, silicate, glass fiber, asbestos, talc, kaolin, mica, barium sulfate, carbon black, carbon fiber, zeolite and a mixture thereof.

Among these additives above, phenol antioxidant, phosphorous antioxidant, ultraviolet absorber, hindered amine photostabilizer, peroxide scavenger and neutralizing agent are preferably used.

Examples of the particularly preferred phenol antioxidant include the following compounds, and they may be used in combination of the two or more:

2,6-di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis(4-ethyl-6-t-butylphenol), 2,2'-methylenebis[4-ethyl-6-(α-methylcyclohexyl)phenol], 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1'-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol, bis[3,3-bis-(3'-t-butyl-4'-hydroxyphenyl)butyrate], 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, 2,4,6-tris(3,5-di-t-butyl-4-phneoxy)-1,3,5-triazine, tris(4-t-butyl-3-hydroxy-2,6-dimethylbenzyl)isocyanurate, tris(3,5-di-t-butyl-4-hydroxybenzyl)isocyanurate, tris[2-(3,',5'-di-t-butyl-4'-hydroxycinnamoyloxy)ethyl]isocyanurate, diethyl-3,5-di-t-butyl-4-hydroxybenzyl phosphonate, di-n-octadecyl-3,5-di-t-butyl-4-hydroxybenzyl phosphonate, calcium salt of 3,5-di-t-butyl-4-hydroxybenzylphosphonic acid monoester, n-octadecyl 3-(3,5-di-t-butyl-4-hydroxyphenyl)propionate, neopentanetetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butylI-4-hydroxy-3-methylcinnamate), 3,9-bis[2-(3-(3-t-butyl-4-hydroxy-5-methylphenyl)propionyloxy)-1,1-dimethylethyl]-2,4,8,10 -tetraoxaspiro [5,5]undecane, N,N'-bis[3-(3',5'-di-t-butyl-4'-hydroxyphenyl)propionyl)] hydrazine, N,N'-bis[3-(3',5'-di-t-butyl-4'-hydroxyphenyl)propionyl]hexamethylenediamine and the like.

Examples of the particularly preferred phosphorous antioxidant include the following, and they may be used in combination of the two or more:

tris(nonylphenyl)phosphite, tris(2,4-di-t-butylphenyl) phosphite, distearyl pentaerythritol diphosphite, bis(2,4-di-t-butylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, tetrakis(2,4-di-t-butylphenyl)-4,4'-diphenylenediphosphite, 2,2'-methylenebis(4,6-di-t-butylphenyl) 2-ethylhexyl phosphite, 2,2'-ethylidenebis(4,6-di-t-butylphenyl) fluorophosphite, bis(2,4-di-t-butyl-6-methylphenyl) ethylphosphite, 2-(2,4,6-tri-t-butylphenyl)-5-ethyl-5-butyl-1,3,2-oxaphospholinane, 2,2',2"-nitrilo[triethyltris(3,3',5,5'-tetra-t-butyl-1,1'-biphenyl-2,2'-diyl)phosphite and the like Examples of the particularly preferred ultraviolet absorber include the following, and two or more kinds of them can be used.

phenyl salicylate, 4-t-butylphenyl salicylate, 2,4 -di-t-butylphenyl 3',5'-di-t-butyl-4'-hydroxybenzoate, 4-t-octylphenyl salicylate, 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone, 2-(2-hydroxy-5-methylphenyl) benzotriazole, 2-(3',5'-di-t-butyl-2'-hydroxyphenyl) benzotriazole, 2-(5'-t-butyl-2'-hydroxyphenyl) benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole and the like Examples of the particularly preferred photostabilizer include the following, and two or more kinds of them can be used.

bis(2,2,6,6-tetramethyl-4-piperidyl)sebacate, bis(1,2,2,6,6-pentamethyl-4-piperidyl)sebacate, bis(N-octoxy-2,2,6,6-pentamethyl-4-piperidyl)sebacate, bis(N-octoxy-2,2,6,6-pentamethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acryloyl-2,2,6,6-tetramethyl-4-piperidyl) 2,2-bis(3,5-di-t-butyl-4-hydroxybenzyl)-2 -butylmalonate, bis(2,2,6,6-tetramethyl-4-piperidyl)succinate, 2,2,6,6-tetramethyl-4-piperidyl methacrylate, 4-[3-(3,5-di-t-butyl-4-hydroxyphenyl) propionyloxy]-1-[2-(3-(3,5-di-t-butyl-4-hydroxyphenyl) propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl)propionamide, tetrakis(2,2,6,6-tetramethyl-4-piperidyl) 1,2,3,4-butanetetracarboxylate, tetrakis(1,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-tetracarboxylic acid and 1,2,2,6,6-pentamethyl-4-piperidinol and 3,9-bis(2-hydroxy-1,1-dimethylethyl)-2,4,8,10-tetraoxaspiro[5,5]undecane, mixed esterified product of 1,2,3,4-butanetetracarboxylic acid and 2,2,6,6-tetramethyl-4-piperidinol and 3,9-bis(2-hydroxy-1,1-dimethylethyl)-2,4,8,10-tetraoxaspiro[5,5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino) hexamethylene ((2,2,6,6-tetramethyl-4-piperidyl)imino)], poly[(6-(1,1,3,3-tetramethylbutyl)imino-1,3,5-triazin-2,4-diyl) ((2,2,6,6-tetramethyl-4-piperidyl)imino) hexamethylene ((2,2,6,6-tetramethyl-4-piperidyl)imino)] and the like When the piperidine compound (I) and optionally used other additives are formulated in the organic material, known any methods and devices for obtaining a homogeneous mixture can be used. For example, when the organic material is a solid polymer, the piperidine compound and other additives can be directly dry-blended in the solid polymer, and the piperidine compound or other additives can also be formulated in the solid polymer in the form of a masterbatch. When the organic material is a liquid polymer, the piperidine compound (I) and other additives can be formulated in the polymer solution during or immediately after polymerization in the form of a solution or a dispersion. On the other hand, when the organic material is a liquid such as oil, the piperidine compound (I) and other additives can also be dissolved by direct addition, and the piperidine compound and other additives can also be added in the form of being dissolved or dispersed in the liquid medium.

The piperidine compound (I) of the present invention is excellent in blooming resistance, exhibits excellent abilities as a light stabilizer for various organic materials including thermoplastic resins such as a polyolefin and the like. An organic material containing this compound is stable against light degradation and the like, and is a product of high quality.

The following examples further illustrate the present invention in detail, but do not limit the present invention.

EXAMPLE 1

Production example of tris(2,2,6,6-tetramethyl-4-piperidyl) 2-stearoyloxy-1,2,3-propanetricarboxylate To a mixture of 12.0 g of tris(2,2,6,6-tetramethyl-4-piperidyl) 2-hydroxy-1,2,3-propanetricarboxylate and 150 ml of toluene was added 2.6 g of triethylamine, subsequently 7.2 g of stearoyl chloride, over a period of 30 minutes respectively, with stirring. Then, the mixture was stirred for 24 hours at room temperature.

To this was added 100 g of 10% sodium carbonate solution, and the mixture was stirred, allowed to stand still, and subjected to separation to obtain an organic phase. Then, lower boiling point fractions were distilled off from the organic phase, and the resulted residue was purified by silica gel chromatography to obtain 10.8 g of a colorless solution.

FD—MS $M^{30}$=876

EXAMPLE 2

A Dry-Blended material described below was extruded by an extruder of 30 mm Φ at 210 to 230° C. into pellets. The resulted pellets was molded by an injection molding machine having mold compressing force of 30 ton at 220 to 240° C., into a plaque of sheet having length of 60 mm, width of 40 mm and thickness of 1 mm. This plaque was stored in a Gear-oven kept at 80° C. for 1 week.

Gloss values of the sheet surface were measured before and after the storage, and blooming resistance was evaluated by retention ratio of the measured data. Results are shown in Table 1. The higher retention ratio means the more excellent blooming resistance. The gloss value was measured by a digital deformation glossmeter (incident angle, light-intercepting angle: 60°) according to JIS K 7105.

<composition>

Non-stabilized polypropylene 100 parts by weight
Calcium stearate 0.05 parts by weight
Tetrakis[methylene-3-(3,5-di-t-butyl-4-hydroxyphenyl) propionate]methane 0.05 parts by weight Tris(2,4-di-t-butylphenyl)phosphite 0.05 parts by weight
Tested Sample 0.2 parts by weight C-1: compound 1 (produced in Example 1)
LS-1: bis(2,2,6,6-tetramethyl-4-piperidyl)sevacate
LS-2: tris(2,2,6,6-tetramethyl-4-piperidyl) 2-hydroxy-1,2,3-propanetricarboxylate

TABLE 1

|  | Example | Comparative example | |
|---|---|---|---|
|  | 1 | 1 | 2 |
| Sample | C-1 | LS-1 | LS-2 |
| Gloss retention ratio (%) | 80 | 29 | 41 |

What is claimed is:

1. A piperidine compound represented by the formula (I):

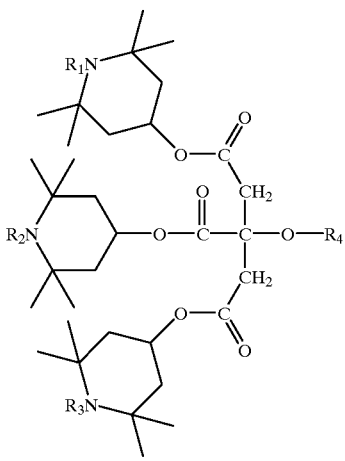

(I)

wherein $R_1$ $R_2$ and $R_3$ each independently represent a hydrogen atom, a lower alkyl group, a cycloalkyl group having 5 to 7 carbon atoms or an acyl group having 2 to 18 carbon atoms, and at least one of $R_1$, $R_2$ and $R_3$ represents an acyl group having 2 to 18 carbon atoms; and $R_4$ represents an acyl group having 2 to 18 carbon atoms.

2. The piperidine compound according to claim 1 wherein $R_4$ is selected from groups represented by the formula (II)

$R_5$—C(O)— (II)

wherein $R_5$ represents an alkyl group having 2 to 17 carbon atoms, a cycloalkyl group having 3 to 9 carbon atoms which may be optionally substituted with a lower alkyl group and/or lower alkenyl group, a phenyl group having 6 to 14 carbon atoms which may be optionally substituted with a lower alkyl group and/or hydroxyl group, or a phenylalkylene group having 7 to 17 carbon atoms in which the phenyl group may be optionally substituted with a lower alkyl group and/or hydroxyl group.

3. A method for producing the piperidine compound according to claim 1, which comprises acylation of a piperidyl hydroxycarboxylate represented by the formula (III):

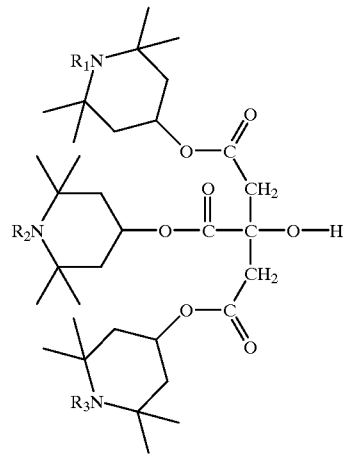

(III)

wherein $R_1$, $R_2$ and $R_3$ are the same as defined in claim 1, with an acylating agent represented by the formula (IV):

$R_4$—X (IV)

wherein $R_4$ is the same as defined in claim 1,

X represents a halogen atom, $OR_7$, —$OC(O)R_5$ or —$NR_8R_9$, wherein $R_5$ represents an alkyl group having 2 to 17 carbon atoms, a cycloalkyl group having 3 to 9 carbon atoms which may be optionally substituted with a lower alkyl group and/or lower alkenyl group, a phenyl group having 6 to 14 carbon atoms which may be optionally substituted with a lower alkyl group and/or hydroxyl group, or a phenylalkylene group having 7 to 17 carbon atoms in which the phenyl group may be optionally substituted with a lower alkyl group and/or hydroxyl group, and $R_7$, $R_8$ and $R_9$ represent a hydrogen atom or lower alkyl group.

4. The method according to claim 3, wherein $R_4$ is selected from groups represented by the formula (II)

$R_5$—C(O)— (II)

wherein $R_5$ represents an alkyl group having 2 to 17 carbon atoms, a cycloalkyl group having 3 to 9 carbon atoms which may be optionally substituted with a lower alkyl group and/or lower alkenyl group, a phenyl group having 6 to 14 carbon atoms which may be optionally substituted with a lower alkyl group and/or hydroxyl group, or a phenylalkylene group having 7 to 17 carbon atoms in which the phenyl group may be optionally substituted with a lower alkyl group and/or hydroxyl group.

5. A stabilizer for an organic material which comprises the piperidine compound according to claim 1.

6. A composition which comprises an organic material and the piperidine compound according to claim 1 and an organic material to be stabilised by the piperidine compound.

7. The piperidine compound according to claim 1 wherein $R_1$ is an acyl group.

8. The piperidine compound according to claim 1 wherein $R_2$ is an acyl group.

9. The piperidine compound according to claim 1 wherein $R_3$ is an acyl group.

10. The piperidine compound according to claim 2 wherein $R_5$ is a phenyl group having 6 to 14 carbon atoms which may be optionally substituted with a lower alkyl group and/or hydroxyl group, or a phenylalkylene group having 7 to 17 carbon atoms in which the phenyl group may be optionally substituted with a lower alkyl group and/or hydroxyl group.

* * * * *